United States Patent

Boese et al.

(10) Patent No.: US 8,488,737 B2
(45) Date of Patent: Jul. 16, 2013

(54) MEDICAL X-RAY IMAGING SYSTEM

(75) Inventors: Jan Boese, Eckental (DE); Jens Fürst, Herzogenaurach (DE); Michael Maschke, Lonnerstadt (DE); Frank Sprenger, Cary, NC (US)

(73) Assignees: Siemens Aktiengesellschaft, München (DE); XinRay Systems LLC, Research Triangle Park, NC (US)

( * ) Notice: Subject to any disclaimer, the term of this patent is extended or adjusted under 35 U.S.C. 154(b) by 295 days.

(21) Appl. No.: 12/967,297

(22) Filed: Dec. 14, 2010

(65) Prior Publication Data

US 2011/0170663 A1    Jul. 14, 2011

(30) Foreign Application Priority Data

Dec. 14, 2009 (DE) .......................... 10 2009 058 266

(51) Int. Cl.
*G01N 23/04* (2006.01)
*H01J 35/02* (2006.01)

(52) U.S. Cl.
USPC ............................................. 378/62; 378/122

(58) Field of Classification Search
USPC ............................................. 378/4, 9, 62, 122
See application file for complete search history.

(56) References Cited

U.S. PATENT DOCUMENTS

| 4,326,144 A | 4/1982 | Appelt | |
|---|---|---|---|
| 5,835,561 A | 11/1998 | Fiekowsky | |
| 7,359,484 B2 | 4/2008 | Lu | |
| 2006/0045234 A1* | 3/2006 | Pelc et al. | 378/9 |
| 2006/0274889 A1* | 12/2006 | Lu et al. | 378/122 |
| 2008/0247503 A1* | 10/2008 | Lauritsch et al. | 378/4 |
| 2009/0067569 A1 | 3/2009 | Baek | |
| 2011/0211666 A1* | 9/2011 | Ying et al. | 378/9 |

FOREIGN PATENT DOCUMENTS

| DE | 102005012700 A1 | 9/2006 |
|---|---|---|
| DE | 102008004473 A1 | 7/2009 |
| WO | WO 2009104156 A1 | 8/2009 |
| WO | WO 2010070554 A1 | 6/2010 |

OTHER PUBLICATIONS

Michael A Speidel et al., "Comparison of vessel contrast measured with a scanning-beam digital x-ray system and an image intensifier/television system", Medical Physics, vol. 28, No. 2, Feb. 2001; pp. 232-240.

* cited by examiner

*Primary Examiner* — Irakli Kiknadze

(57) ABSTRACT

In order to achieve improved image quality in X-ray photographs, a medical X-ray imaging system, comprising a flat, planar X-ray source having a surface with X-ray focal points arranged adjacent to one another and an X-ray detector with a sensor surface, is provided. The X-ray source has a plurality of field emission guns with at least one field emission cathode and the surface with focal points of the X-ray source is larger in size than the sensor surface of the X-ray detector.

11 Claims, 2 Drawing Sheets

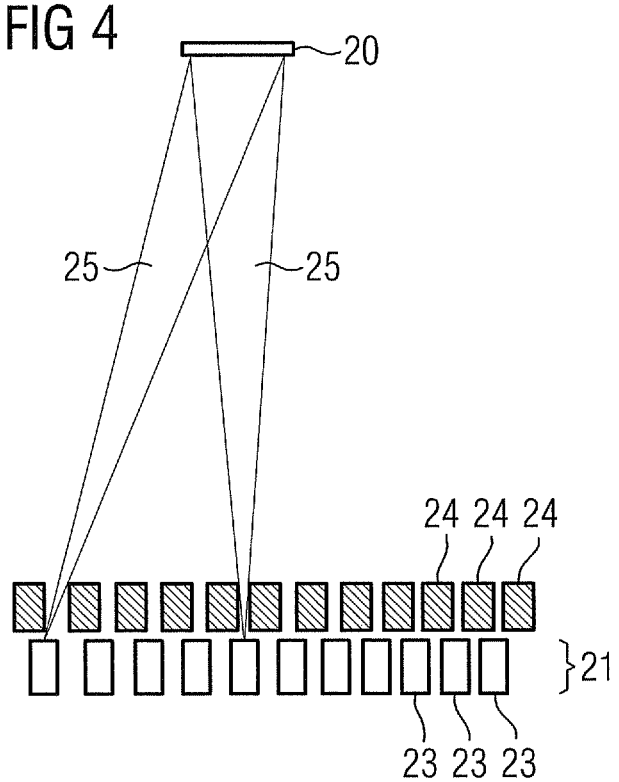

MEDICAL X-RAY IMAGING SYSTEM

CROSS REFERENCE TO RELATED APPLICATIONS

This application claims priority of German application No. 10 2009 058 266.5 filed Dec. 14, 2009, which is incorporated by reference herein in its entirety.

FIELD OF THE INVENTION

The invention relates to a medical X-ray imaging system.

BACKGROUND OF THE INVENTION

Vacuum tubes have been used for decades in the well-known medical X-ray technology field as X-ray sources for generating ionizing X-radiation. In these applications an electron beam is emitted from a metal filament cathode heated to over 1000° C. in an evacuated glass tube and accelerated toward a metal anode made, for example, of tungsten, as a result of which X-radiation is generated. A vacuum tube of said kind having a rotating anode is known from U.S. Pat. No. 4,326,144, for example. Known vacuum tubes have among other things the disadvantages of heavy weight (both due to their intrinsic weight and due to an additionally necessary water cooling system), large dimensions, a low level of efficiency, and in particular significant heat generation.

New interventional X-ray applications impose increasingly exacting demands in terms of image quality; at the same time it is important to keep exposure of patients and staff to X-radiation to a minimum. According to the prior art conventional X-ray emitters and flat-panel X-ray detectors are currently used for interventional X-ray systems. Limiting factors affecting image quality in this case are, inter alia, scattered radiation and the limited efficiency of the detector.

SUMMARY OF THE INVENTION

It is the object of the present invention to provide a medical X-ray imaging system which ensures the recorded X-ray images are of a high quality.

The object is achieved according to the invention by a medical X-ray imaging system as claimed in the independent claim. Advantageous embodiments of the invention are in each case the subject matter of the associated dependent claims.

The medical X-ray imaging system according to the invention has a flat, planar X-ray source having a surface with X-ray focal points arranged adjacent to one another and an X-ray detector having a sensor surface, the X-ray source having a plurality of field emission guns with at least one field emission cathode and the surface with focal points of the X-ray source being larger in size than the sensor surface of the X-ray detector. The X-ray imaging system according to the invention has what is termed an inverse geometry, as a result of which the scattered radiation, for example, is significantly reduced, thereby lowering the exposure to radiation for patient and operator as well as increasing image quality. In contrast to known X-ray emitters, the field emission guns can be produced efficiently and economically in large numbers and with very small dimensions and used cost-effectively. Instead of a large X-ray detector, a relatively small, though at the same time very powerful and efficient X-ray detector is used, as a result of which the image quality of the recorded X-ray images can likewise be improved. What is to be understood by the surface with the focal points of the X-ray source is the two-dimensional area over which the field emission guns are distributed, the field emission guns or, more accurately, their focal points being arranged as densely as possible.

In a field emission cathode, electrons are emitted as a result of a sufficiently high electric field being applied. Field emission is achieved e.g. by means of a simple diode mode in which a bias voltage is applied between anode and cathode. Electrons are emitted from the cathode when the electric field exceeds the threshold for the emission. A triode construction can also be provided in which a gate electrode is arranged close to the cathode. Electrons are emitted in this case as a result of a bias voltage being applied between gate and cathode. The emitted electrons are then accelerated by means of a high voltage between gate and anode. Field emission cathodes permit a very high, readily controllable and easily focusable electron beam current. Furthermore, the electron beam can also be deflected magnetically or electrostatically.

Overall, by virtue of the field emission guns the invention has the advantages of low heat generation by the X-ray source and a low weight, attributable not only to the field emission guns themselves but also to the omission or reduction in size of a cooling system. Compared with conventional X-ray emitters, field emission guns are also extremely compact, which is a prerequisite for making a high-quality, planar X-ray source having a surface of many focal points arranged adjacent to one another possible in the first place. This is ensured in particular by an array having a plurality of field emission guns. The lifespan of field emission guns is also significantly longer than that of known X-ray emitters with thermal cathodes. Compared with a thermal cathode, a field emission cathode can also be started quickly without heating. By virtue of the easily focusable electron current a higher spatial resolution can additionally be achieved for X-ray images. All in all, an X-ray source having field emission guns is also particularly suitable for new applications in which rapid movements of the X-ray source or of the entire imaging systems consisting of X-ray source and X-ray detector are necessary.

According to an embodiment of the invention the field emission cathode in each case has a nanostructured material with carbon nanotubes (a so-called CNT cathode). Materials of this kind exhibit particularly good emission characteristics, are stable even at high currents, and furthermore can be manufactured in a particularly small format. Alternatively the field emission cathodes can also have nanocrystalline graphite.

The surface of the X-ray source is advantageously at least twice, in particular between twice and eight times, as large in size as the sensor surface of the X-ray detector. This enables the advantages of the inverse geometry to be exploited to optimal effect. The X-ray detector is beneficially formed by a digital flat-panel detector.

According to another embodiment of the invention the field emission guns are arranged on a surface in a rectangular, elliptical or circular array.

The X-ray source and X-ray detector are advantageously carried jointly by a C-arm or U-bracket. Such a C-arm or U-bracket can also be arranged on a multi-axis robot arm, in particular on an articulated arm robot having six axes of rotation, so that it can be moved along any trajectories.

According to further embodiments of the invention the X-ray imaging system is formed by a fluoroscopy system or an angiography system or a projection X-ray system.

BRIEF DESCRIPTION OF THE DRAWINGS

The invention and other advantageous embodiments according to features of the dependent claims are explained in more detail below with reference to schematically illustrated exemplary embodiments in the drawing, without this implying any limitation of the invention to said exemplary embodiments.

FIG. 4 shows a side view of an emitter array with collimators.

DETAILED DESCRIPTION OF THE INVENTION

Figure 1:
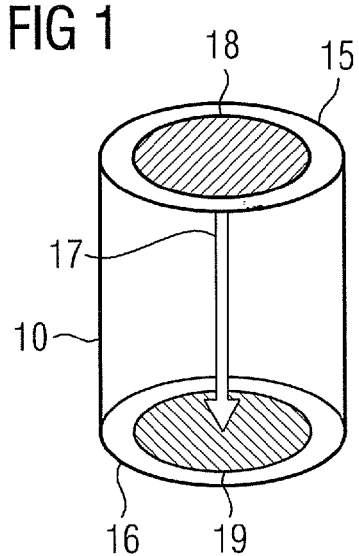
FIG. 1 shows a view of a field emission gun with one field emission cathode.

FIG. 1 shows a field emission gun 10 with a cathode 15 having a (single) electron-emitting element 18 and an anode 16 having a (single) focal point 19. In this case the material that is particularly well suited as a cathode for generating the high electron current densities necessary is carbon, in particular in the form of nanotubes (CNT cathode). By application of a corresponding electric field the electron-emitting element 18 is stimulated without heating to emit an electron beam 17 which subsequently strikes the anode 16 or, as the case may be, focal point 19 and generates X-radiation there.

Figure 2:
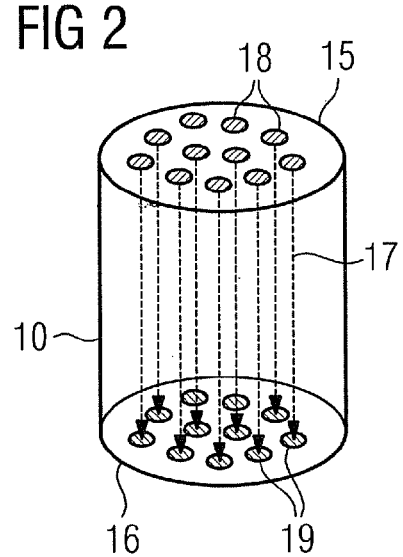
FIG. 2 shows a view of a field emission gun with a plurality of field emission cathodes.

FIG. 2 shows a further embodiment of a field emission gun 10 which has a cathode having a plurality of electron-emitting elements 18, all of which can be activated individually. In this case the elements 18 can be arranged in the manner of pixels. The anode 16 too consists of a plurality of focal points 19, each electron-emitting element 18 being assigned a focal point 19. The anode can consist, for example, of copper, tungsten, molybdenum or an alloy of the same. A gate electrode (not shown) can also be arranged between the cathode and the anode in order to provide better control of the electron emission from the cathode. The electron beam can also be deflected magnetically or electrostatically. In this way it is possible to target a plurality of focal points in succession with a reduced number of electron-emitting elements; an electron-emitting element can therefore be assigned more than one focal point.

Figure 3:
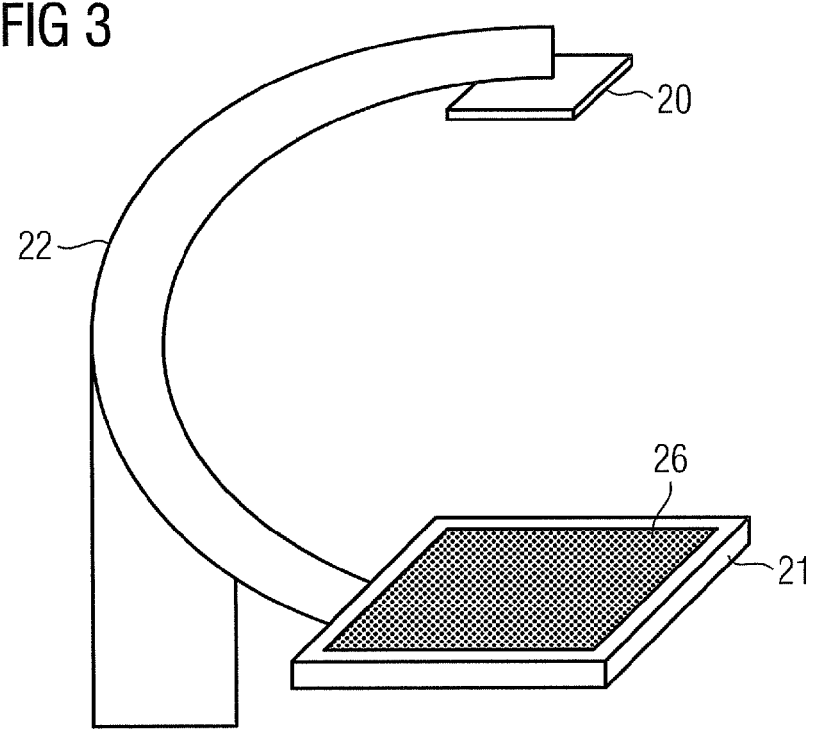
FIG. 3 shows a view of an inventive X-ray imaging system with inverse geometry.

FIG. 3 shows a detail from an inverse-geometry X-ray imaging system according to the invention having a C-arm 22 for carrying an X-ray detector 20 and an array 21 consisting of field emission guns. The C-arm 22 can be carried, for example, by means of an articulated arm robot and be displaced three-dimensionally in space. In this arrangement the array 21 of field emission guns is constructed in particular in a rectangle shape, i.e. the field emission guns are arranged in such a way that the focal points are distributed in particular uniformly over an in particular rectangular surface 26. This can appear on the one hand in such a way that a large number of small field emission guns each having one focal point are arranged distributed in particular uniformly over the surface or in such a way that a plurality of field emission guns each having a plurality of focal points are arranged uniformly distributed over the surface 26. The focal points can be arranged in the manner of pixels, for example. The X-ray detector 20 is embodied in such a way that its active surface is significantly smaller, in particular between one half and one eighth, of the surface area of the field emission guns. The X-ray detector is in particular a digital flat-panel detector based on amorphous silicon.

One of the advantages of the so-called inverse geometry of the X-ray imaging system, in other words an X-ray source extending over a greater surface area in proportion to the X-ray detector, is, for example, a reduction in the radiation dose for patients and operators.

FIG. 4 shows a side view of the X-ray imaging system with its beam geometry. An arrangement of collimators 24 is positioned in front of the array 21 of field emission guns in order to form the respective X-radiation. In particular, parts of the X-radiation are masked out so that only the X-ray beams 25 that strike the X-ray detector 20 are allowed through.

The array 21 can have around 100×100 field emission guns and collimators, for example. A complete X-ray image is generated in that each field emission gun is activated for a short time and the associated single image is read out. All the single images are then reconstructed, e.g. by means of tomosynthesis reconstruction, to create a 3D volume. For that purpose very short exposure times per single image are necessary. If it is aimed to record the total volume in 10 ms (this is e.g. a typical exposure time in angiography), the 10,000 single images have an exposure time of one microsecond only. Such short exposure times can be achieved particularly easily with field emission guns. Furthermore, an X-ray imaging system made up of field emission guns can be implemented as a compact, lightweight and low-cost solution. In particular the lower weight of the field emission guns in conjunction with a digital flat-panel detector reduces the moving masses of the device during the different types of examination. A further advantage is the long useful life and low heat generation of such field emission guns.

The invention can be briefly summarized as follows: In order to achieve improved image quality in X-ray photographs, a medical X-ray imaging system, comprising a flat, planar X-ray source having a surface with X-ray focal points arranged adjacent to one another and an X-ray detector with a sensor surface, is provided, the X-ray source having a plurality of field emission guns with at least one field emission cathode and the surface with focal points of the X-ray source being larger in size than the sensor surface of the X-ray detector.

The invention claimed is:
1. A medical X-ray imaging system, comprising:
a flat, planar X-ray source having a surface;
a field emission gun arranged on the X-ray source comprising a cathode and an anode; and
an X-ray detector having a sensor surface,
wherein the surface of the X-ray source is larger than the sensor surface of the X-ray detector,
wherein the X-ray source comprises an array having a plurality of field emission guns, and
wherein the field emission guns are arranged in a rectangular array, an elliptical array, or a circular array such that the field emission guns are distributed uniformly over the surface of the X-ray source.

2. The X-ray imaging system as claimed in claim 1, wherein the surface of the X-ray source is at least twice as large as the sensor surface of the X-ray detector.

3. The X-ray imaging system as claimed in claim 1, wherein the cathode comprises an electron-emitting element.

4. The X-ray imaging system as claimed in claim 3, wherein the anode comprises a focal point.

5. The X-ray imaging system as claimed in claim 1, wherein the cathode comprises a plurality of electron-emitting elements that are activated individually.

6. The X-ray imaging system as claimed in claim 5, wherein the anode comprises a plurality of focal points arranged adjacent to one another that correspond to the electron-emitting elements respectively.

7. The X-ray imaging system as claimed in claim 1, wherein the cathode comprises a nanostructured material with carbon nanotubes.

8. The X-ray imaging system as claimed in claim 1, wherein the X-ray detector is a digital flat-panel detector.

9. The X-ray imaging system as claimed in claim 1, wherein the X-ray source and the X-ray detector are carried jointly by a C-arm or a U-bracket.

10. The X-ray imaging system as claimed in claim 9, wherein the X-ray source and/or the X-ray detector or the C-arm or the U-bracket are arranged on an articulated arm robot.

11. The X-ray imaging system as claimed in claim 1, wherein the X-ray imaging system is selected from a group consisting of: a fluoroscopy system, an angiography system, and a projection X-ray system.

* * * * *